(12) United States Patent
Vigliante

(10) Patent No.: US 7,085,349 B2
(45) Date of Patent: Aug. 1, 2006

(54) X-RAY DIFFRACTOMETER FOR HIGH FLUX GRAZING INCIDENCE DIFFRACTION

(75) Inventor: Assunta Vigliante, Stuttgart (DE)

(73) Assignee: Bruker AXS GmbH, Karlsruhe (DE)

( * ) Notice: Subject to any disclaimer, the term of this patent is extended or adjusted under 35 U.S.C. 154(b) by 21 days.

(21) Appl. No.: 10/819,234

(22) Filed: Apr. 7, 2004

(65) Prior Publication Data

US 2004/0228440 A1 Nov. 18, 2004

(30) Foreign Application Priority Data

May 14, 2003 (EP) .................................. 03010763

(51) Int. Cl.
*G01N 23/20* (2006.01)
(52) U.S. Cl. .............................. 378/71; 378/79; 378/81
(58) Field of Classification Search ............. 378/70–89
See application file for complete search history.

(56) References Cited

U.S. PATENT DOCUMENTS

| | | | |
|---|---|---|---|
| 3,852,594 A * | 12/1974 | Paolini ........................ | 378/81 |
| 5,214,685 A | 5/1993 | Howells | |
| 6,301,330 B1 * | 10/2001 | Kurtz et al. .................. | 378/71 |
| 6,385,289 B1 * | 5/2002 | Kikuchi ........................ | 378/79 |
| 2002/0160305 A1 | 10/2002 | Horie | |
| 2003/0009316 A1 | 1/2003 | Yokoyama | |
| 2004/0066894 A1 * | 4/2004 | Holz et al. ..................... | 378/84 |

OTHER PUBLICATIONS

"Advanced Thin film X-ray system-Grazing incidence in-plane diffractometer". The Rigaku Journal, vol. 16, No. 1 (1999).
Sakata, O. et al. "Ultrahigh-vacuum facility for high- resolution grazing-angle x-ray diffraction at a vertical wiggler source of synchrotron radiation." J. of Synch. Rad., Jul. 1, 1998, Munksgaard, Denmark.
Daillant J. et al. "High-Resolution X-ray scattering Experiments: I. Surfaces", Rep. Prog. Phys., vol. 63, 2000, pp. 1725-1777.

* cited by examiner

*Primary Examiner*—Edward J. Glick
*Assistant Examiner*—Krystyna Suchecki
(74) *Attorney, Agent, or Firm*—Paul Vincent

(57) ABSTRACT

An X-ray diffractometer (1) comprising an X-ray source (2) emitting a line focus X-ray beam (3; 11) wherein the larger extension of the beam cross section defines a line direction (4; 12) of the X-ray beam (3; 11), further comprising a sample (6; 13), and an X-ray detector (7) rotatable in a scattering plane around an axis ω intersecting the position of the sample (7) is characterized in that the X-ray source is mounted to a switching device (10), which allows to move the X-ray source into one of two fixed positions with respect to the scattering plane, wherein in the first position the line direction (4) of the X-ray beam (3) is parallel to the scattering plane and in the second position the line direction (12) of the X-ray beam (11) is perpendicular to the scattering plane, and wherein the path of the X-ray beam (3, 11) in the two fixed positions of the X-ray source is the same. This X-ray diffractometer has a simple mechanical setup and allows in plane grazing incidence diffraction as well as regular XRD measurements with good resolution.

16 Claims, 3 Drawing Sheets

X-RAY DIFFRACTOMETER FOR HIGH FLUX GRAZING INCIDENCE DIFFRACTION

This application claims Paris Convention priority of EP 03 010 763.5 filed May 14, 2003 the complete disclosure of which is hereby incorporated by reference.

BACKGROUND OF THE INVENTION

The invention relates to an X-ray diffractometer comprising an X-ray source emitting a line focus X-ray beam having an aspect ratio of the beam cross section perpendicular to the propagation direction of at least 1.5, preferably >2, wherein the larger extension of the beam cross section defines a line direction of the X-ray beam, further comprising a sample, and an X-ray detector rotatable in a scattering plane around an axis ω intersecting the position of the sample (="2Θ-movement of the detector").

An X-ray diffractometer of this type is disclosed by in The Rigaku Journal, Vol. 16, No. 1, 1999, pages 53–58, describing the commercially available "ATX-G" diffractometer.

X-ray diffraction is a powerful tool for material characterization. Various measurement techniques have been developed for analyzing different material properties. In thin film technology, grazing incidence diffraction (GID) is used to obtain information from the near-surface region of a sample and/or the in plane orientation of a crystalline sample.

A typical GID setup includes an X-ray source, typically with a collimator, a flat sample and a detector. The incident angle of the X-ray beam arriving at the sample is low, typically less than 1°.

Another set-up used for GID consists of a standard high resolution X-ray diffractometer with horizontal scattering geometry equipped with Eulerian cradle, a point focus X-ray source or alternatively a vertically shaped X-ray line source followed by a small (~1 mm) pin collimator and an X-ray detector moving in the horizontal plane of scattering. This configuration has the advantage of a multipurpose instrument, since many different measurements can be performed (e.g. high resolution, stress, texture and GID), but yields low X-ray intensity.

Regular X-ray diffractometer setups used for GID use an X-ray source emitting a substantially horizontal X-ray beam with a vertical X-ray line direction, a substantially horizontally oriented flat sample and an X-ray detector moving in a horizontal plane. Thus, the sample surface and the line direction of the X-ray beam are substantially perpendicular. The projection of the X-ray beam on the sample is spread over a wide area then, resulting in a low usable X-ray intensity and a poor resolution. Note that for regular measurements, i.e. non-GID measurements such as theta-2theta scans, the flat sample is vertically oriented, leading to a small projection of the X-ray beam on the sample surface, and the regular X-ray diffractometer setup results in good resolution then.

In order to get better intensity for GID applications, powerful rotating anodes are used.

An increase of X-ray flux in an in-plane GID measurement can also be obtained by the use of an X-ray line source with its line direction parallel to the sample surface (which is substantially parallel to the scattering plane in this setup, wherein the scattering plane is defined as the plane in which the detector can move). Compared to a setup wherein the line direction is perpendicular to the sample surface, this geometry increases the flux by reducing the size of the effective projection (footprint) of the X-ray beam on the sample surface. Thus a significant improvement of the scattered X-ray intensity for GID can be obtained.

In the above mentioned "ATX-G" diffractometer, a line shaped X-ray beam with its line direction extending in a vertical direction is directed onto a flat sample. For GID measurements, the sample is also vertically oriented to increase the X-ray flux. In order to be able to measure the in-plane orientation of the sample in this geometry, an X-ray detector is movable in a vertical plane. In addition, the X-ray detector is also movable in a horizontal plane for performing regular measurements in high flux geometry, so the ATX-G is designed as a six circle diffractometer.

The ATX-G is disadvantageous in that the six-circle setup is expensive and difficult to calibrate and to control. Moreover, the vertically oriented sample position also limits the sample materials that can be measured by in-plane GID. Samples which cannot be turned in such a position are excluded from a measurement.

It is the underlying purpose of the invention to provide an X-ray diffractometer with which high flux in-plane GID measurements as well as regular X-ray measurements with good resolution can be performed and wherein the X-ray diffractometer has a simple mechanical setup.

SUMMARY OF THE INVENTION

This object is achieved by an X-ray diffractometer as mentioned above, characterized in that the X-ray source is mounted to a switching device, which allows to move the X-ray source into one of two fixed positions with respect to the scattering plane, wherein in the first position the line direction of the X-ray beam is substantially parallel to the scattering plane and in the second position the line direction of the X-ray beam is substantially perpendicular to the scattering plane, and wherein the path of the X-ray beam in the two fixed positions of the X-ray source is substantially the same.

By means of the invention, the X-ray diffractometer can be operated in two setup positions representing different, perpendicular line direction orientations of the X-ray beam. The line direction of the X-ray beam relative to the sample surface can be chosen independent from the sample orientation. In turn, the sample orientation can be chosen, in accordance with the desired type of measurement, with respect to the movement plane of the detector. Therefore only one movement plane for the detector, e.g. a horizontal movement plane, is sufficient for performing all types of measurements (i.e. in-plane GID and regular) with good resolution. In other words, a simple four circle diffractometer design of the inventive X-ray diffractomer has full versatility for all types of measurements. After having chosen the sample orientation with respect to the movement plane of the detector, the line direction of the X-ray beam can be adapted by means of the switching device. Usually, this adaptation will be setting the line direction of the X-ray beam parallel to the sample surface (i.e. the sample surface normal and the line direction are perpendicular) in order to increase the X-ray flux.

The first position of the X-ray source is particularly suited for performing high flux in-plane GID measurements, wherein the reflecting planes in the sample are substantially perpendicular to the sample surface. In contrast, the second position represents a position that can be used for most other XRD measurement techniques, e.g. theta-2theta scans, wherein the reflecting planes are typically (but not necessarily) parallel to the sample surface. In accordance with the invention, the X-ray diffractometer can comprise a sample switching means for turning the sample (or a corresponding sample holder, respectively) when changing the fixed position of the X-ray source. The sample switching means keeps the sample surface parallel to the line direction of the X-ray beam. For this purpose, the sample switching means can be coupled to the switching device.

In a preferred embodiment of the inventive X-ray diffractometer, the movement of the switching device is remotely controlled, in particular by use of an electric motor. The X-ray source is typically an item of considerable weight, and moving the X-ray source by hand may be too difficult for an operator of low strength. The use of a motor allows the use of the embodiment by every operator regardless of strength. Moreover, the positioning of the X-ray source can be performed with higher reproducibility.

Also preferred is an embodiment wherein the switching device comprises mechanical references for defining the two fixed positions of the X-ray source, in particular end stops and/or guiding rails. The end stops can be realized as reference pins. The mechanical references increase the reproducibility of the positioning of the X-ray source.

In a further development of this embodiment, the mechanical references comprise locking means keeping the X-ray source in either one of the two fixed positions. The locking means increase the reproducibility and stability of the two fixed positions of the X-ray source.

Also within the scope of the present invention is an X-ray diffractometer comprising an X-ray source emitting a line focus X-ray beam having an aspect ratio of the beam cross section perpendicular to the propagation direction of at least 1.5, preferably >2, wherein the larger extension of the beam cross section defines a line direction of the X-ray beam, further comprising a sample, and an X-ray detector rotatable in a scattering plane around an axis ω intersecting the position of the sample (="2Θ-movement of the detector"), characterized in that the scattering plane is horizontally oriented and that the line direction of the X-ray beam is substantially parallel to the scattering plane.

This latter inventive X-ray diffractometer is particularly suited for in-plane GID measurements. In in-plane GID, the scattering plane and the sample surface are substantially parallel. Due to the resulting parallel orientation of the line direction of the X-ray beam and the sample surface, high flux is achievable during in-plane GID measurements. At the same time, the sample surface is horizontally oriented during this in-plane GID.

This means that samples which are sensitive to the forces of gravity can be investigated for in-plane GID with the inventive X-ray diffractometer. Samples sensitive to the forces of gravity include liquid samples such as liquid crystals, or samples showing significant creep or recrystallization influenced by forces of gravity during the measurement. The inventive X-ray diffractometer can also be used with mechanically unstable samples, i.e. with samples that cannot be fixed to a sample holder by clamping or gluing without being destroyed during fixing or removing, e.g. due to low fracture toughness. In accordance with the invention, the sample only needs to be laid down with the flat side up.

Of course, the inventive latter X-ray diffractometer may be equipped with an inventive switching device as described above.

A further preferred embodiment of an inventive X-ray diffractometer is characterized in that the sample is mounted on an Eulerian cradle. An Eulerian cradle is a well known diffraction tool for X-ray crystallography.

Particularly preferred is an embodiment wherein a multilayer mirror, in particular a Göbel mirror, is arranged in the path of the X-ray beam between the X-ray source and the sample. The multilayer mirror allows a high intensity parallelization of the X-ray beam at low divergence perpendicular to line direction.

An advantageous further development of this embodiment is characterized in that a beam collimator is arranged in the path of the X-ray beam between the multilayer mirror and the sample. The beam collimator reduces the beam size and therewith the background signal for small samples.

Alternatively or in addition, in another preferred further development, a monochromator, in particular a beam compressor or a channel cut, is arranged in the path of the X-ray beam between the multilayer mirror and the sample. This provides a good energy and spatial resolution.

An advantageous further embodiment of an inventive X-ray diffractometer is characterized in that at least one Soller slit is arranged in the path of the X-ray beam between the X-ray source and the sample. The Soller slit reduces the X-ray beam divergence. In accordance with the invention, a Soller slit can also be placed between the sample and the X-ray detector, alternatively or in addition.

In a highly preferred embodiment, the sample has a flat surface which is horizontally oriented. This makes the X-ray diffractomer inherently suitable for liquid samples such as liquid crystals or suspensions, or for electrochemistry.

Also advantageous is an embodiment wherein the X-ray source is mounted rotatably around an axis v which is perpendicular to the ω axis. This offers an additional degree of freedom with liquid samples.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

The invention is shown in the drawing.

BRIEF DESCRIPTON OF THE DRAWING

DESCRIPTION OF THE PREFERRED EMBODIMENT

Figure 1A:
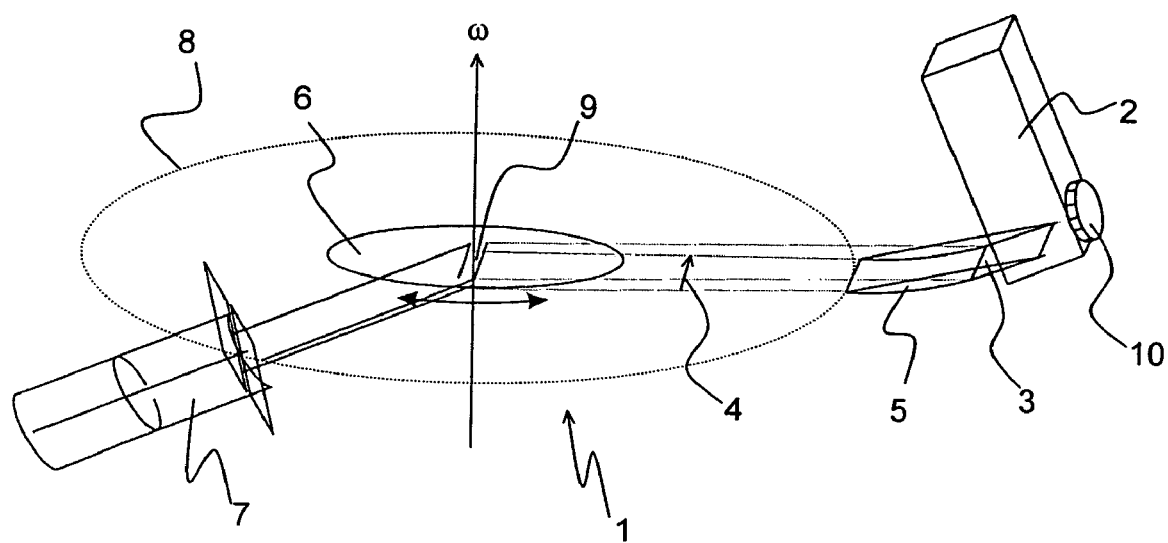
FIG. 1a shows an X-ray diffractometer with a rotatable X-ray source in a first position in accordance with the invention.

FIG. 1a shows an inventive X-ray diffractometer 1 in a first position of an X-ray source 2 used for in plane grazing incidence diffraction (GID). The X-ray source 2 comprises an X-ray sealed tube and can be rotated by means of a switching device 10 from the first position shown in FIG. 1a, wherein it stands upright, to a second position shown in FIG. 1b later on.

The X-ray source 2 emits a line focused X-ray beam 3, with its line direction 4 oriented horizontally, i.e. extending from front to back in FIG. 1a. The X-ray beam 3 has a substantially rectangular shape, wherein the line direction 4 coincides with the direction of the long sides of the rectangle. Note that another possible shape of the X-ray beam 3 is an ellipsoid, wherein the long axis defines the line direction 4.

The X-ray beam 3 is focused by a Göbel mirror 5 onto a sample 6. The sample 6 has a flat disc-shaped surface, wherein the sample surface is horizontally oriented, i.e. the plane of the disc is horizontally oriented, with its plane normal extending vertically. The incidence angle of the X-ray beam 3 on the surface of the sample 6 is about 0.5°, typical for a GID geometry. This incidence angle is neglected in the figures, however. The line direction 4 of the X-ray beam 3 is parallel to the sample surface of the sample 6, keeping a projection 9 of the X-ray beam 3 on the sample 6 small. This increases the effective X-ray flux.

The X-ray beam 3 is diffracted at the sample 6 by reflection planes within the sample which are substantially vertically oriented. The diffracted X-ray beam 3 is detected by an X-ray detector 7. The X-ray detector 7 is a scintillator detector and can be rotated around an axis ω on a circular curve 8. The circular curve 8 defines the movement plane of the X-ray detector 7, referred to as the scattering plane. The scattering plane in FIG. 1a is horizontally oriented, representing a preferred orientation of the X-ray diffractometer 1 as a whole. The axis ω intersects the position of the sample 6.

Positions of the X-ray detector 7 where signal is detected in a GID measurement can be used to determine the absolute orientation of the responsible reflecting plane within the sample 6, since the bisecting line of the angle between incident and outgoing X-ray beam 3 indicates the plane normal of the reflecting plane. The type of the reflection plane can be estimated e.g. by Bragg's equation.

Figure 1B:
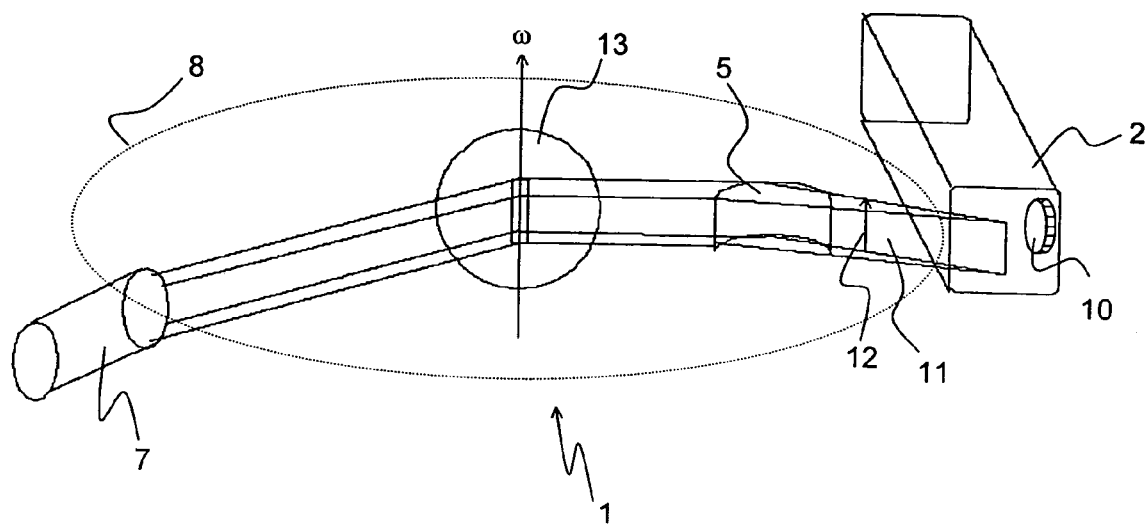
FIG. 1b shows the X-ray diffractometer of FIG. 1a with the rotatable X-ray source in a second position in accordance with the invention.

FIG. 1b shows the inventive X-ray diffractometer 1 of FIG. 1a in a second position of the X-ray source 2 used for regular XRD measurements such as a theta-2theta scan. The second position of the X-ray source 2 is arrived at by operating the switching device 10.

The X-ray source 2 lies on a long side. It emits a line shaped X-ray beam 11, with its line direction 12 extending vertically. The X-ray beam 11 is focused by the Göbel mirror 5 onto a sample 13. Note that the Göbel mirror 5 may be rigidly linked to the X-ray source in order to be adequately positioned in both first and second position of the X-ray source 2. Note that the general direction of propagation of the X-ray beam 11 directly behind the X-ray source 2 is identical to the general direction of propagation of the X-ray beam 3 directly behind the X-ray source 2 in FIG. 1a.

The sample 13 has again a flat disc-shaped surface. The sample 13 is vertically oriented so that again the line direction 12 of the X-ray beam 11 is parallel to the surface of the sample 13 in order to keep the effective beam size small and the resolution high. In contrast to FIG. 1a, the incidence angle of the X-ray beam 11 on the sample 13 is not restricted. For a theta-2theta scan, the incidence angle theta is scanned from typically about 1° to 180°.

The X-ray beam 11 is then diffracted by reflection planes of the samples. In case of a theta-2theta scan, these reflection planes are parallel to the surface of the sample 13, i.e. the reflection planes-are vertically oriented. The X-ray detector 7 detects the diffracted X-ray beam 11. Note that during a theta-2theta scan, both the sample 13 and the X-ray detector 7 are rotated around a vertical axis intersecting with the sample 13, but with the double angular velocity of the X-ray detector 7 compared to the sample 13.

By means of the invention, it is therefore possible to use an X-ray detector 7 movable exclusively in one movement plane (here the horizontal plane) for performing both in-plane GID measurements as well as regular XRD measurements such as theta-2theta scans with the line direction of the incoming X-ray beam parallel to the sample surface. This allows high flux in both cases.

Figure 2:
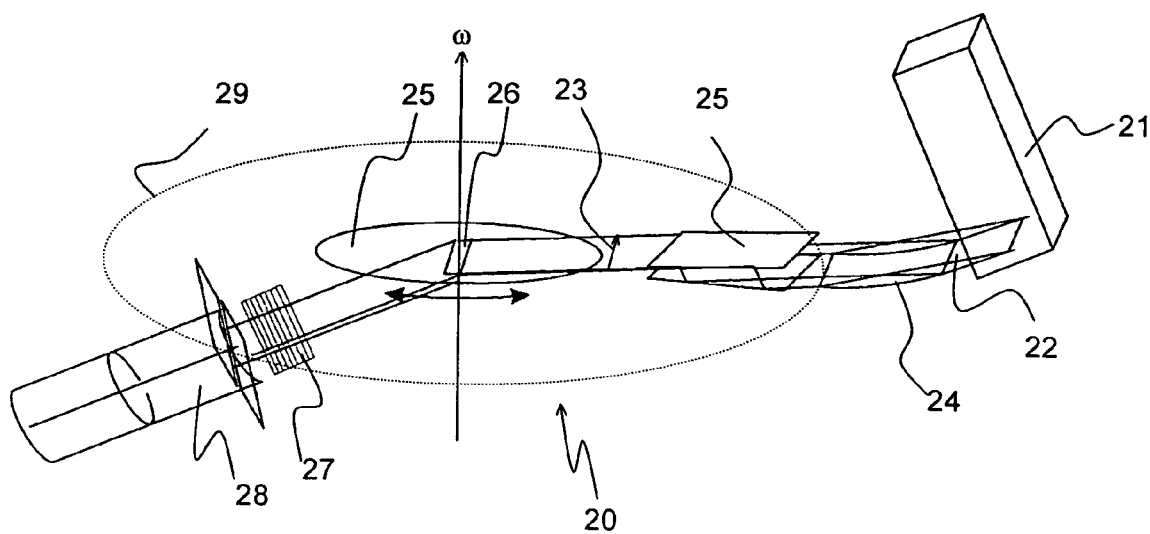
FIG. 2 shows an X-ray diffractometer with a horizontal scattering plane and a line direction of an X-ray beam parallel to the scattering plane in accordance with the invention.

FIG. 2 shows another inventive X-ray diffractometer 20 dedicated to in-plane GID measurements, with a horizontal scattering plane and a line direction of an X-ray beam parallel to the scattering plane. An X-ray source 21 as an X-ray sealed tube emits a line focused X-ray beam 22 with a horizontal line direction 23. The X-ray beam 22 is shaped by a Göbel mirror 24 and a beam compressor 25 and hits a sample 25. The sample 25 has a flat horizontal surface and is round. The incident angle of the X-ray beam 22 on the sample 25 is very small, typically smaller than 5°, preferably smaller than 1°. Due to the line direction 23 being parallel to the surface of the sample 25, the projection 26 of the X-ray beam 22 on the sample 25 is relatively small. This allows high resolution in-plane GID measurements. The X-ray beam 22 is then diffracted at vertically oriented reflection planes within the sample 25. After passing a set of Soller slits 27, the diffracted X-ray beam 22 is detected in an X-ray detector 28 such as a scintillator detector. The X-ray detector 28 can be moved on a curve 29 around a vertical axis ω in a movement plane, the so-called scattering plane. The scattering plane is horizontally oriented.

The X-ray diffractometer of FIG. 2 is different from the X-ray diffractometers of the state of the art in that it allows an in-plane GID measurement with a line direction 23 of an X-ray beam 22 parallel to the surface of a flat sample 25 to be investigated, wherein the sample 25 is horizontally oriented during the measurement. This makes the inventive X-ray diffractometer suitable for high flux in-plane GID measurements of liquid samples, in particular liquid crystals.

I claim:

1. An X-ray diffractometer for analysis of a sample, the diffractometer comprising:
    an X-ray source emitting a line focus X-ray beam having an aspect ratio of a beam cross section, perpendicular to a propagation direction, of at least 1.5, wherein a larger extension of said beam cross section defines a line direction of said X-ray beam;
    an X-ray detector rotatable in a scattering plane around an axis ω intersecting the sample; and
    a switching device cooperating with said X-ray source to move said X-ray source into a first position in which said line direction of said X-ray beam is substantially parallel to said scattering plane and into a second position in which said line direction of said X-ray beam is substantially perpendicular to said scattering plane and substantially parallel to said axis ω, wherein a path of said X-ray beam is substantially unchanged between said first and said second positions.

2. The X-ray diffractometer of claim 1, wherein said aspect ratio is >2.

3. The X-ray diffractometer of claim 1, further comprising means for remotely controlling a movement of said switching device.

4. The X-ray diffractometer of claim 3, wherein said remotely controlling means comprises an electric motor.

5. The X-ray diffractometer of claim 1, wherein said switching device comprises mechanical references for defining said first and said second positions of said X-ray source.

6. The X-ray diffractometer of claim 5, wherein said mechanical references comprise end stops and/or guiding rails.

7. The X-ray diffractometer of claim 5, wherein said mechanical references comprise locking means keeping said X-ray source in either one of said first and said second positions.

8. The X-ray diffractometer of claim 1, further comprising an Eulerian cradle on which the sample is mounted.

9. The X-ray diffractometer of claim 1, further comprising a multilayer mirror disposed in a path of said X-ray beam between said X-ray source and the sample.

10. The X-ray diffractometer of claim 9, wherein said multilayer mirror comprises a Goebel mirror.

11. The X-ray diffractometer of claim 9, further comprising a beam collimator disposed in said path of said X-ray beam between said multilayer mirror and the sample.

12. The X-ray diffractometer of claim 9, further comprising a monochromator disposed in said path of said X-ray beam between said multilayer mirror and the sample.

13. The X-ray diffractometer of claim 12, wherein said monochromator is one of a beam compressor and a channel cut.

14. The X-ray diffractometer of claim 1, further comprising at least one Soller slit disposed in a path of said X-ray beam between said X-ray source and the sample.

15. The X-ray diffractometer of claim 1, wherein the sample has a horizontally oriented, flat surface.

16. The X-ray diffractometer of claim 1, wherein said X-ray source is mounted to rotate about an axis $\psi$ which is substantially within said scattering plane which intersects the sample.

* * * * *